United States Patent [19]
Berg et al.

[11] Patent Number: 5,227,029
[45] Date of Patent: Jul. 13, 1993

[54] SEPARATION OF FORMIC ACID FROM ACETIC ACID BY EXTRACTIVE DISTILLATION

[75] Inventors: Lloyd Berg, 1314 S. Third Ave., Bozeman, Mont. 59715; Randi W. Wytcherley, Bozeman, Mont.

[73] Assignee: Lloyd Berg, Bozeman, Mont.

[21] Appl. No.: 11,233

[22] Filed: Jan. 29, 1993

[51] Int. Cl.$^5$ .................. B01D 3/40; C07C 53/02; C07C 51/44
[52] U.S. Cl. .................. 203/51; 203/57; 203/61; 562/608; 562/609
[58] Field of Search ............. 203/51, 57, 61; 562/608, 609

[56] References Cited

U.S. PATENT DOCUMENTS

| | | | |
|---|---|---|---|
| 3,394,058 | 7/1968 | Hohenschutz | 203/15 |
| 3,437,566 | 4/1969 | Gasser et al. | 562/609 |
| 3,660,483 | 5/1972 | Hobbs et al. | 562/608 |
| 3,801,629 | 4/1974 | Aga et al. | 562/608 |
| 4,110,372 | 8/1978 | Hey et al. | 562/608 |
| 4,576,683 | 3/1986 | Cohen | 562/608 |
| 4,692,219 | 9/1987 | Berg | 203/51 |
| 4,909,907 | 3/1990 | Berg | 203/51 |

*Primary Examiner*—Wilbur Bascomb, Jr.

[57] ABSTRACT

Formic acid cannot be easily removed from formic acid-acetic acid mixtures by distillation because of the closeness of their boiling points. Formic acid can be readily removed from mixtures containing it and acetic acid by extractive distillation. Typical effective agents are 2-nitrotoluene, 1-nitropropane and m-nitrobenzoic acid.

1 Claim, No Drawings

SEPARATION OF FORMIC ACID FROM ACETIC ACID BY EXTRACTIVE DISTILLATION

FIELD OF THE INVENTION

This invention relates to a method for separating formic acid from acetic acid using certain higher boiling liquids as the agent in extractive distillation.

DESCRIPTION OF PRIOR ART

Extractive distillation is the method of separating close boiling compounds or azeotropes by carrying out the distillation in a multi-plate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boils twenty Centigrade degrees or more higher than the lowest boiling component.

At the bottom of a continuous column, the less volatile components of the close boiling mixture and the extractive agent are continuously removed from the column. The usual methods of separation of these two components are the use of another rectification column, cooling and phase separation or solvent extraction.

Extractive distillation would be an attractive method of effecting the separation of formic acid from acetic acid if agents can be found that (1) will create a large apparent relative volatility between formic and acetic acids and (2) are easy to recover from acetic acid, that is, form no azeotrope with acetic acid and boil sufficiently above acetic acid to make the separation by rectification possible with only a few theoretical plates.

Extractive distillation typically requires the addition of one half the amount to twice as much extractive agent as the formic-acetic acids on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required if the separation is done by azeotropic distillation. Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is desirable that the extractive agent be miscible with acetic acid otherwise it will form a two-phase azeotrope with acetic acid in the recovery column and some other method of separation will have to be employed.

L. Berg, U.S. Pat. No. 4,692,219 described the use of straight chain carboxylic acids from hexanoic to neodecanoic as the agent in the separation of formic acid from acetic acid by extractive distillation.

Formic acid, B.P. 101° C. and acetic acid, B.P. 118° C. have a relative volatility of 1.2 and are difficult to separate by conventional rectification. Table 1 shows that to get 99% purity, 68 actual plates are required. For an agent giving a relative volatility of 1.4, 37 actual plates are required and with a relative volatility of 2.0, only seventeen actual plates are required

TABLE 1

Theoretical and Actual Plates Required vs. Relative Volatility for Formic Acid-Acetic Acid Separation

| Relative Volatility | Theoretical Plates Required At Total Reflux, 99% Purity | Actual Plates Required, 75% Eff. |
|---|---|---|
| 1.2 | 51 | 68 |
| 1.4 | 28 | 37 |
| 1.6 | 20 | 27 |
| 1.8 | 16 | 21 |
| 2.0 | 13 | 17 |

OBJECTIVE OF THE INVENTION

The object of this invention is to provide a process or method of extractive distillation that will enhance the relative volatility of formic acid to acetic acid in their separation in a rectification column. It is a further object of this invention to identify organic compounds which in addition to the above constraints, are stable, can be separated from acetic acid by rectification with relatively few theoretical plates and can be recycled to the extractive distillation column and reused with little decomposition.

SUMMARY OF THE INVENTION

The objects of this invention are provided by a process for separating formic acid from acetic acid which entails the use of certain nitrogen containing organic compounds as the agent in extractive distillation.

DETAILED DESCRIPTION OF THE INVENTION

We have discovered that certain nitrogen containing organic compounds will greatly improve the relative volatility of formic acid to acetic acid and permit the separation of formic acid from acetic acid by rectification when employed as the agent in extractive distillation.

TABLE 2

Effective Extractive Distillation Agents

| Compounds | Relative Volatility |
|---|---|
| None | 1.2 |
| Nitrobenzene | 1.7 |
| 2-Nitrotoluene | 1.7 |
| 3-Nitrotoluene | 1.7 |
| 4-Nitrotoluene | 1.4 |
| 1-Nitropropane | 1.7 |
| 2-Nitropropane | 1.6 |
| 3-Nitroxylene | 1.5 |
| m-Nitrobenzoic acid | 1.6 |
| 4-Nitrotoluene, 2-Nitrotoluene | 1.5 |
| 4-Nitrotoluene, 3-Nitrotoluene | 1.4 |
| 4-Nitrotoluene, Nitrobenzene | 1.4 |
| m-Nitrobenzoic acid, 2-Nitrotoluene | 1.6 |
| m-Nitrobenzoic acid, 2-Nitropropane | 1.6 |

Table 2 lists the compounds that we have found to be effective. They are nitrobenzene, 2-nitrotoluene, 3-nitrotoluene, 4-nitrotoluene, 3-nitroxylene, 1-nitropropane, 2-nitropropane and m-nitrobenzoic acid. The data in Table were obtained in a vapor-liquid equilibrium still. 4-Nitroxyluene and m-nitrobenzoic acid, although effective extractive distillation agents in the pure state, are high melting solids which are difficult to handle in distillation equipment. The data determined for them in mixtures shows how they can best be obtained in the liquid state and still retain most of their effectiveness.

A series of runs were made with the agent 2-nitrotoluene in which the ratio of formic acid to acetic acid was varied. One run was made at a reduced pressure of 150 mm Hg. These data are presented in Table 3 and show that the relative volatility remained consistently high.

TABLE 3

Effect of Ratio and Pressure on the Separation of Formic Acid from Acetic Acid Using 2-Nitrotoluene as the Agent

| Ratio: Formic acid | Acetic acid | Relative Volatility | |
|---|---|---|---|
| 85 | 15 | 1.5 | |
| 70 | 30 | 1.6 | |
| 50 | 50 | 1.7 | |
| 50 | 50 | 1.7 | *Reduced pressure |
| 30 | 70 | 2.1 | |
| 15 | 85 | 2.1 | |

THE USEFULNESS OF THE INVENTION

The usefulness or utility of this invention can be demonstrated by referring to the data presented in Tables 1 and 2. All of the successful agents show that formic acid can be separated from acetic acid by means of extractive distillation in a rectification column and that the ease of separation as measured by relative volatility is considerable.

WORKING EXAMPLES

Example 1

Thirty grams of formic acid, 70 grams of acetic acid and 50 grams of 2-nitrotoluene were charged to an Othmer type vapor-liquid equilibrium still and refluxed for 3 hours. Analysis of the vapor and liquid by gas chromatography gave a vapor composition of 36.1% formic acid, 63.9% acetic acid and a liquid cmposition of 21.6% formic acid, 78.4% acetic acid. This indicates a relative volatility of 2.1.

Example 2

Eighty grams of formic acid, 20 grams of acetic acid, 25 grams of m-nitrobenzoic acid and 25 grams of 2-nitropropane were charged to the vapor-liquid equilibrium equilibrium still and refluxed for ten hours. Analysis gave a vapor composition of 85.1% formic acid, 14.9% acetic acid and a liquid composition of 77.5% formic acid, 22.5% acetic acid. This indicates a relative volatility of 1.6.

We claim:

1. A method for recovering formic acid from a mixture of formic acid and acetic acid which comprises distilling a mixture of formic acid and acetic acid in a rectification column in the presence of about one part of an extractive agent per part of formic acid-acetic acid mixture, recovering formic acid as overhead product and obtaining the acetic acid and the extractive agent from the stillpot, wherein said extractive agent consists of a material selected from the group consisting of 2-nitrotoluene, 3-nitrotoluene, 4-nitrotoluene, 3-nitroxylene, 1-nitropropane, 2-nitropropane, m-nitrobenzoic acid and mixtures thereof.

* * * * *